US009011964B1

(12) United States Patent
Zeng

(10) Patent No.: US 9,011,964 B1
(45) Date of Patent: Apr. 21, 2015

(54) NANO-ENCAPSULATED, CONTROLLED DRUG MANUFACTURING PROCESS

(71) Applicant: Albert S. Zeng, Cupertino, CA (US)

(72) Inventor: Albert S. Zeng, Cupertino, CA (US)

(73) Assignee: Albert S. Zeng, Cupertino, CA (US)

( * ) Notice: Subject to any disclaimer, the term of this patent is extended or adjusted under 35 U.S.C. 154(b) by 0 days.

(21) Appl. No.: 14/562,708

(22) Filed: Dec. 6, 2014

(51) Int. Cl.
*A61K 9/00* (2006.01)
*A61K 9/51* (2006.01)
*A61K 38/02* (2006.01)
*A23K 1/00* (2006.01)

(52) U.S. Cl.
CPC .............. *A61K 9/5192* (2013.01); *A61K 38/02* (2013.01); *A61K 9/0034* (2013.01); *A23K 1/002* (2013.01)

(58) Field of Classification Search
CPC ........... A61K 38/02; A61K 9/20; A61K 9/22; A61K 9/14; A61K 38/54; A61K 38/43; A61K 35/74; A61K 31/122; B01F 15/0238
See application file for complete search history.

(56) References Cited

U.S. PATENT DOCUMENTS

| 2005/0186273 A1* | 8/2005 | Yum et al. ...................... 424/464 |
| 2011/0306539 A1* | 12/2011 | Shen et al. ...................... 514/1.1 |
| 2014/0030031 A1* | 1/2014 | Stevenson et al. ............ 406/127 |

* cited by examiner

*Primary Examiner* — Dah-Wei D Yuan
*Assistant Examiner* — Andrew Bowman
(74) *Attorney, Agent, or Firm* — Jingming Cai; Schein & Cai LLP

(57) ABSTRACT

A mixed dose of a nanosized drug wherein at least one portion of the mixed dose comprises a core nanosized drug encapsulated in at least one layer of a protective material having the same core drug or different core drug. A mixed dose of a nanosized drug wherein at least one portion of the mixed dose comprises a core nanosized drug encapsulated in at least one shell of a protective material with same drug concentration or different drug concentrations. A mixed dose of a nanosized drug wherein at least one portion of the mixed dose comprises a core nanosized drug encapsulated such that it has different release schedule than other portions of the drug. Methods and systems for manufacturing and administration of nanosized encapsulated drugs are also provided.

14 Claims, 4 Drawing Sheets

←100

←101

←102

←103

NANO-ENCAPSULATED, CONTROLLED DRUG MANUFACTURING PROCESS

CROSS REFERENCE TO RELATED APPLICATIONS

This application is a continuation-in-part application of patent application Ser. No. 14/072,137 titled "Nano-encapsulated, controlled drug delivery, manufacturing process and system" filed on Nov. 5, 2013 in the United States Patent and Trademark Office, which is a divisional application of patent application Ser. No. 13/775,016 titled "Nano-encapsulated, controlled drug delivery, manufacturing process and system" filed on Feb. 22, 2013 in the United States Patent and Trademark Office.

The specifications of the above referenced patent applications are incorporated herein by reference in their entirety.

BACKGROUND

The system and manufacturing process disclosed herein, in general, relates to nanobiopharmaceutics. More particularly, the system and manufacturing process disclosed herein relates to nano-encapsulated drugs, their controlled and/or scheduled delivery method, manufacturing process, and processing of nanosized, delivery controlled encapsulated drugs.

Traditional medicine administered orally may have a slower and less complete absorption than medicine administered using parenteral (non-oral) routes. Dissolution of solid formulations (e.g., tablets) must occur first. The drug must survive exposure to stomach acid and this route of administration is subject to first pass effect (metabolism of a significant amount of the drug in gut wall and liver), before it reaches the systemic circulation where it can take effect.

Even if it reaches the systemic circulation, the route of the drug is completely random. It may flow around and be expelled from the body without performing its job.

Because it is hard for the drug to find its desired target, a good amount of the drug is wasted, and a large amount of the medicine must be administrated, increasing toxicity in the body and causing unnecessary medicine waste. More damaging is that, by circulating throughout the body looking for a target, and by increasing the toxicity level of the body, these traditional medicines kill both good cells and bad cells.

In addition, the traditional drugs/medicines are expelled out of the body in a very short time period, which is why some medicines need to be taken multiple times a day for several days. An example is Amoxicillin, which may need to be taken every 6 hours per day, 7 days per treatment session.

In summary, traditional drugs have low effectiveness and efficiency, they may require repeated administration, they cause high levels of body toxicity, and they are expensive.

One of the challenges of pharmaceutical research is to discover tools and methods enabling an effective and efficacious delivery of drugs into tissues or organs where the drugs are needed, and in addition, scheduling delivery of the drugs in a controlled manner.

Nanomedical approach to drug delivery centers on developing nanoscaled particles or molecules to improve drug bioavailability. Bioavailability refers to the presence of drug molecules where they are needed in the body, where they will do most good, and over a desired period of time. More than $65 billion are wasted each year due to poor bioavailability of existing drugs. Thus, drug delivery research focuses on maximizing bioavailability both at specific places in the body and over a period of time.

Protein and peptides exert multiple biological actions in a human body and they have been identified as showing great promise for treatment of various diseases and disorders. These macromolecules are called biopharmaceuticals. Targeted and/or controlled delivery of these biopharmaceuticals using nanomaterials like nanoparticles and dendrimers is an emerging field called nanobiopharmaceutics, and these products are called nanobiopharmaceuticals.

Two forms of nanomedicine that have already been tested in mice and are apparently awaiting human trials is using gold nanoshells to help diagnose and treat cancer, and using liposomes as vaccine adjuvants and as vehicles for drug transport.

It has been seen that drug detoxification is another application for nanomedicine which has shown promising results in rats. A benefit of using nanoscale for medical technologies is that smaller devices are less invasive and can possibly be implanted inside the body. In addition, biochemical reaction times are much shorter. These devices are faster and more sensitive than typical drug delivery.

This strategy took the fashionable name of 'nanomedicine' (medical application of nanotechnology), mainly based on the use of lipid-based (liposomes) and polymer-based (nanoparticles or NPs) nano-carriers or metal-based nano-vectors. An example of nano-carriers i.e., super-paramagnetic NPs is currently used in medicine in order to improve quality and specificity of body/cell imaging and diagnostics. These carriers are usually made of gold or iron, comprising a core-shell able to be visualized within the body, thus allowing the physician to obtain better-defined contrast and diagnostic images (http://www.futuremedicine.com/doi/pdf/10.2217/nnm.12.90).

Nano-encapsulated drugs are nanosized packages of drugs that are encapsulated/covered with layer(s) such as liposomes and/or polymer or other biodegradable protective materials, that protect the drugs inside (core drugs) from unfavorable environments and prevent the drug from taking effect until the capsule dissolves. The cover or coating can delay the drug release. Liposomes and other lipid-based nanocapsules cannot be applied to many drugs. Other than liposomes, no other nanocapsules are known to be available due to difficulty of manufacturing them.

Thus, there is a need for development of new medicine, namely nanosized encapsulated medicines, capable of providing time controlled delivery, and which are easier to administer to target area, require fewer administrations, have lower toxicity, and are less expensive overall. Furthermore, since making nanosized encapsulated medicine is very challenging, there is also a need for providing processes, procedures, and systems to make nanosized encapsulated medicines possible.

Further, the process steps of "deposition" and "etching" are well known in the semiconductor industry in integrated circuit fabrication (http://highered.mcgraw-hill.com/sites/dl/free/0073106941/443736/chapter13.pdf and http://www.nature.com/nmatjournal/v2/n1/fig_tab/nmat768_F4.html).

In this disclosure, applicant has applied concepts from the above two well known technologies in the art (nanotechnology and semiconductor) to arrive at a novel method of manufacture of nanosized encapsulated drugs. Since the applicant's disclosure combines two well known technologies in the art, it will be easily implementable by a person with ordinary skill in these arts The problems and associated solutions presented in this section could be or could have been pursued, but they are not necessarily approaches that have been previously conceived or pursued. Therefore, unless otherwise indicated, it should not be assumed that any of the approaches presented in this section qualify as prior art merely by virtue of their presence in this section of the application.

SUMMARY OF THE INVENTION

This summary is provided to introduce a selection of concepts in a simplified form that are further described below in the detailed description. This summary is not intended to identify key aspects or essential aspects of the claimed subject matter. Moreover, this summary is not intended for use as an aid in determining the scope of the claimed subject matter.

In one exemplary embodiment, a system for manufacturing nanosized encapsulated drugs is provided. In another exemplary embodiment, a process for manufacturing nanosized encapsulated drugs is provided. In another exemplary embodiment, nanosized encapsulated drugs having different protective layers in terms of number of layers, layer thickness and materials used, are provided. In another exemplary embodiment, mixed layered encapsulated drug with same core drug or different core drugs, and having same or different concentrations, is provided.

Thus, it is now possible to efficiently and effectively manufacture nanosized encapsulated drugs capable of providing time controlled delivery with the same or different core drugs and which are easier to administer to target area, require fewer administrations, have lower toxicity, and are less expensive overall.

The above embodiments and advantages, as well as other embodiments and advantages, will become apparent from the ensuing description and accompanying drawings.

BRIEF DESCRIPTION OF THE DRAWINGS

The foregoing summary, as well as following detailed description of the invention, is better understood when read in conjunction with the appended drawings. For purpose of illustrating the invention, exemplary constructions of the invention are shown in the drawings. However, the invention is not limited to the specific methods and components disclosed herein.

DETAILED DESCRIPTION OF THE INVENTION

Figure 1:
FIG. 1 illustrates sectional views of non-coated nanosized medicine, and coated nanosized medicine having one, two and three protective layers, according to several embodiments.
Figure 1:
Figure 1:
Figure 1:
Figure 1:
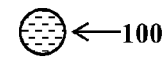
Figure 1:
Figure 1:
Figure 1:
Figure 1:
Figure 1:
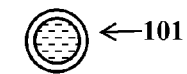
Figure 1:
Figure 1:
Figure 1:
Figure 1:
Figure 1:
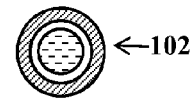
Figure 1:
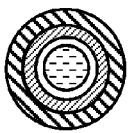
Figure 1:
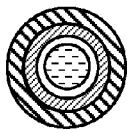
Figure 1:
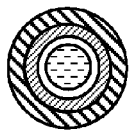
Figure 1:
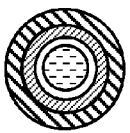
Figure 1:
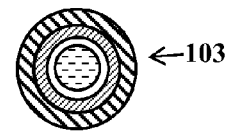

What follows is a detailed description of the preferred embodiments of the invention in which the invention may be practiced. Reference will be made to the attached drawings, and the information included in the drawings is part of this detailed description. The specific preferred embodiments of the invention, which will be described herein, are presented for exemplification purposes, and not for limitation purposes.

It should be understood that structural and/or logical modifications could be made by someone of ordinary skill in the art without departing from the scope of the invention. Therefore, the scope of the invention is defined by the accompanying claims and their equivalents.

For the purpose of this disclosure, the protective material that constitutes the coating layer(s) for the core nanodrug may be a polymer or any other suitable biodegradable material. The protective material can be for example biodegradable polymers and/or bioadhesive polymers.

Examples of biodegradable polymers include synthetic polymers such as poly hydroxy acids, such as polymers of lactic acid and glycolic acid, polyanhydrides, poly(ortho) esters, polyesters, polyurethanes, poly(butyric acid), poly(valeric acid), poly(caprolactone), poly(hydroxybutyrate), poly (lactide-co-glycolide) and poly(lactide-co-caprolactone), and natural polymers such as alginate and other polysaccharides, collagen, chemical derivatives thereof (substitutions, additions of chemical groups, for example, alkyl, alkylene, hydroxylations, oxidations, and other modifications routinely made by those skilled in the art), albumin and other hydrophilic proteins, zein, modified zein, chitin, chitosan, and other prolamines and hydrophobic proteins, copolymers and mixtures thereof (http:///www.google.com/patents/US20080299204).

The bioadhesive polymeric material is selected from a group consisting of polyamides, polyalkylene glycols, polyalkylene oxides, polyvinyl alcohols, polyvinylpyrrolidone, polyglycolides, polyurethanes, polymers of acrylic and methacrylic esters, polylactides, poly butyric acid, group polyanhydrides, polyorthoesters, poly fumaric anhydride, blends, and copolymers thereof (http://www.google.com/patents/US20080299204).

In certain embodiments, the bioadhesive polymeric material is poly fumaric-co-sebacic anhydride (http://www.google.com/patents/US20080299204).

In certain embodiments, the bioadhesive polymeric material comprises a catechol moiety. For example, the bioadhesive polymeric material may comprise a mixture of a polymeric material and a compound comprising a catechol moiety selected from L-dopa, D-dopa, dopamine, or carbidopa. In addition, the bioadhesive polymeric material may be selected from polyamides, polycarbonates, polyalkylenes, polyalkylene glycols, polyalkylene oxides, polyalkylene terephthalates, polyvinyl alcohols, polyvinyl ethers, polyvinyl esters, polyvinyl halides, polyvinylpyrrolidone, polyglycolides, polysiloxanes, polyurethanes, polystyrene, polymers of acrylic and methacrylic esters, polylactides, poly(butyric acid), poly (valeric acid), poly(lactide-co-glycolide), polyanhydrides, polyorthoesters, poly(fumaric) anhydride, blends and copolymers thereof (http://www.google.com/patents/US20080299204).

In certain embodiments, the bioadhesive polymeric material is covalently functionalized with a catechol moiety, such as one derived from L-dopa, D-dopa, dopamine, or carbidopa (http://www.google.com/patents/US20080299204).

In a preferred embodiment, the protective material is selected from a group of aliphatic polymers comprising polyhydroxyl butyrate, polycaprolactone, and/or their copolymers.

For the purpose of this disclosure, the configuration(s) of the material that constitutes the coating layer(s) for the core nanodrug means physical and/or chemical construction, physical and/or chemical formations, physical staggering, and so on.

As stated earlier, nano-encapsulated drugs are nanosized packages of drugs that are encapsulated/covered with layer(s)

such as liposomes and/or polymer or other biodegradable protective materials, that protect the drugs inside (core drugs) from unfavorable environments and prevent the drug from taking effect until the capsule dissolves. The cover or the coating can delay the drug release. More importantly by mixing such coated nanosized drugs, as it will be described herein, the total half life of the drug may be increased.

For the purpose of this disclosure, examples of core drugs available in the market that are suitable for nano-encapsulation are listed in below Table-1 (http://web.archive.org/web/20131206061730/http://www.medscape.com/viewarticle/770 397_2).

TABLE 1

Representative examples of core drugs on the market suitable for nano-encapsulation.

| Type of nanostructure | Brand name | Active ingredient | Indications |
|---|---|---|---|
| Nanocrystalline drugs | Rapamune ® | Rapamycin | Immunosuppressive |
| | Emend ® | Aprepitant | Anti-emetic |
| | Tricor ® | Fenofibrate | Hypercholesterolemia |
| | Megace ® | Megestrol | Anti-anorexia |
| Liposomes | AmBisome ® | Amphotericin B | Fungal infections |
| | Doxil ® | Doxorubicin | Ovarian cancer, Kaposi's sarcoma and breast cancer |
| | Caelyx ® | Doxorubicin | Ovarian cancer, Kaposi's sarcoma and breast cancer |
| | Depocyt ® | Cytarabine | Lymphomatous meningitis |
| | Daunoxome ® | Daunorubicin | Kaposi's sarcoma |
| Polymer-drug conjugates | Adagen ® | Adenosine deaminase | Adenosine deaminase enzyme deficiency |
| | Onscaspar ® | L-asparaginase | Acute lymphoblastic leukemia |
| | Pegasys ® | PEGylated IFN-α-2a | Hepatitis C |
| Polymeric micelles | Genexol-PM ® | Paclitaxel | Cancer chemotherapy |
| Protein (albumin) nanoparticles | Abraxane ® | Paclitaxel | Metastatic breast cancer |
| Lipid colloidal dispersion | Amphotec ® | Amphotericin B | Fungal infections |

In a preferred embodiment, the core drug is selected from one of doxorubicin, topotecan, and paclitaxel (all are cancer treatment drugs) (http://www.liposomeexpert.com/categories/drug-loaded-liposomes.html).

Referring now to FIG. 1, a group of non-coated nanosized drug particles 100 is shown, together with groups of nanosized encapsulated drugs having one 101, two 102 or three 103 protective layers, according to several embodiments. It should be apparent that more than three protective layers may be used for the purposes described herein.

Figure 2:
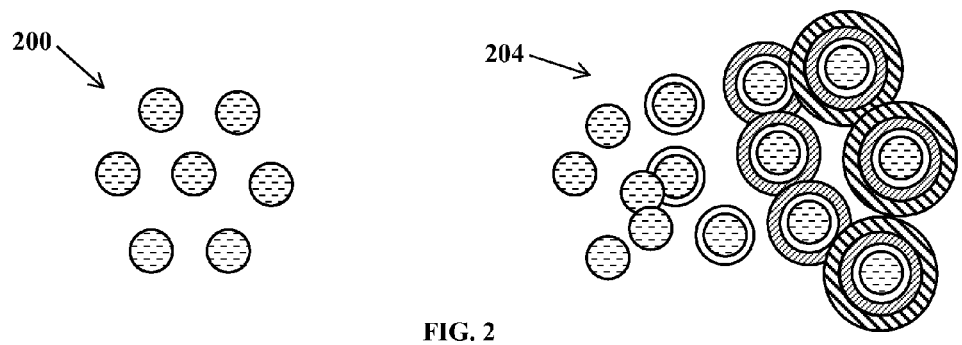
FIG. 2 illustrates sectional views of doses of non-coated nanosized medicine and mixed nanosized encapsulated medicine, according to several embodiments.

In FIG. 2, is shown, a dose of non-coated nanosized drugs 200 and a mixed dose 204 of nanosized drugs including non-coated, one-layer, two-layer and three-layer nano-encapsulated drugs. The mixed dose 204, according to an embodiment, may have nanocapsules with protective layers which are different in terms of number of protective layers, thickness and materials used. Thus, after mixing, longer, scheduled delivery of the drug may be obtained by using protective layers as it will be explained in more details hereafter. Having a portion of non-coated nanosized drugs in a mixed dose 204 may be preferred in most situations to ensure immediate drug action by the non-coated portion. However, the mixed dose 204 may contain only coated nanocapsules when the purpose is to delay any drug action (e.g., by one week) after the administration of the mixed dose.

Here are some exemplary scenarios that may help understand the inventions disclosed herein:

First scenario: Let's assume a dose of a specific nano-encapsulated drug contains nanocapsules having a single shell/bi-layer liposome and an X (e.g., 4-5 nm) nanometer thick polymer layer. The nano-encapsulated drug is administered to the patient. For the purpose of this example, let's assume that its half life time inside the human body is about one week. The drug will stay inside the human body for about three weeks.

Second scenario: If the polymer thickness of the single bi-layer liposome nanocapsules is doubled to 2X nanometers and such nanocapsules are combined/mixed with nanocapsules having a single bi-layer liposome and a single X nm polymer layer, the expected half life time of the mixed dose can be increased to around two weeks. The mixed dose can be expected to last inside of the body around six weeks. Nanocapsulation of the polymers in this case may have to be compressed, meshed, smashed, or nested to certain physical formation or configuration to achieve protection of the Liposomes (to prevent the Liposome from dissolving) or to prevent the core drug from leaking before the scheduled time frame.

The above scenarios, given as examples, show that the half life time and the presence/duration or release time of the nanocapsules can be increased as desired, by increasing the number of protective layers, and/or the thickness of the protective layer(s), and/or by selecting a suitable coating material for the protective layer(s), and/or by suitably altering the physical configuration, structure or construction of the protective layer(s) of the nanocapsules such as by smashing, meshing, compressing or nesting techniques. Thus, to control the time of presence/release and the half life of a nano-encapsulated drug dose administered into the human body, the dose have mixed half life time nanocapsules, with different release schedules.

Mixed nanocapsules, having various number of layers and/or layer thickness, and/or layer material, and/or physical configuration of the protective layers will control when to release the drug, will allow to mix or combine different release times of the drugs, will increase total half life time of the drug, and also provide the possibility of varying drug delivery concentration at specific periods of time. For example, if, when the mixed nanodose is initially prepared and administered, it is anticipated that during the second week of the treatment, more concentrated drug(s) will be needed in the body or in the ill tissue in order to achieve effective treatment given the known behavior of the disease, the concentration of the nano-drug(s) scheduled for release during the second week may be increased in the mixed nanodose. Thus, a mixed nanodose 204 (FIG. 2) may have various components (e.g., non-coated, one-layer, two-layer nanodrug, etc) in equal or different concentrations, with the same, different or a combination of core nanodrug in each component, depending on the delivery schedule desired and/or the treatment objectives.

Mixed nanocapsules, having various layer materials, number of layers and/or layer thickness, and/or physical configuration of the protective layers will thus control when to release the drug, will allow to mix or combine different release time of the drugs, will increase total half life time of the same drug, and also provide the possibility of varying drugs and delivery at specific periods of time. For example, if, after a surgery, first time period needs to stop bleeding, second time period needs to control the possible infections, and third time period needs to cure left over un-cleared tumors, but there is also the need to strengthen the patient by adding nutrition all the time, then mixed drugs can be scheduled such that during first time period the drug to stop bleeding is released, during the second time period the drug to control the possible infections is released, and during the third time period the drug to cure left over un-cleared tumors is released, while nutrition is released all the time.

Thus, besides the nature (materials used), the number of layers and/or the thickness of the protective layers (e.g., polymer, or other bio-degradable material), other factors will control the half life time and the release time or duration of the presence (presence-duration) of the nanodrug in the human body. Examples of such factors are the doping material used if any, or the composition and/or the physical structure of the protective layer(s). All of these factors together will determine when, where and how the nanocapsules will dissolve and when the drug will take effect. Thus, controlling these factors during the manufacturing of the nanodrug will translate into time control of the nanodrug delivery.

The scheduled drug delivery may be further understood by using the example that follows. Let's assume that a mixed dose contains three different categories/types of nanodrugs A1, A2 and A3, in terms of number of layers, thickness and/or nature of the protective material used for the protective layer(s), and/or protective layer(s) physical configuration. The differences in thicknesses, number of layers of protective material and/or materials used, and/or material configurations cause the different nanocapsules to have different release times. For example, if drug A1 releases during the first week, drug A2 releases during the second week and drug A3 releases during the third week. When mixed together, the different release times result in a continuous release time over a period of three weeks.

If the above example is extended to "n" drugs, if drugs (A1, A2, A3, A4, A5 . . . An) are mixed together and administrated, theoretically, the resulting release time of the drug can be about "n" weeks.

What follows are considerations regarding the processes and systems for the manufacturing of nanosized encapsulated drugs.

Figure 4:
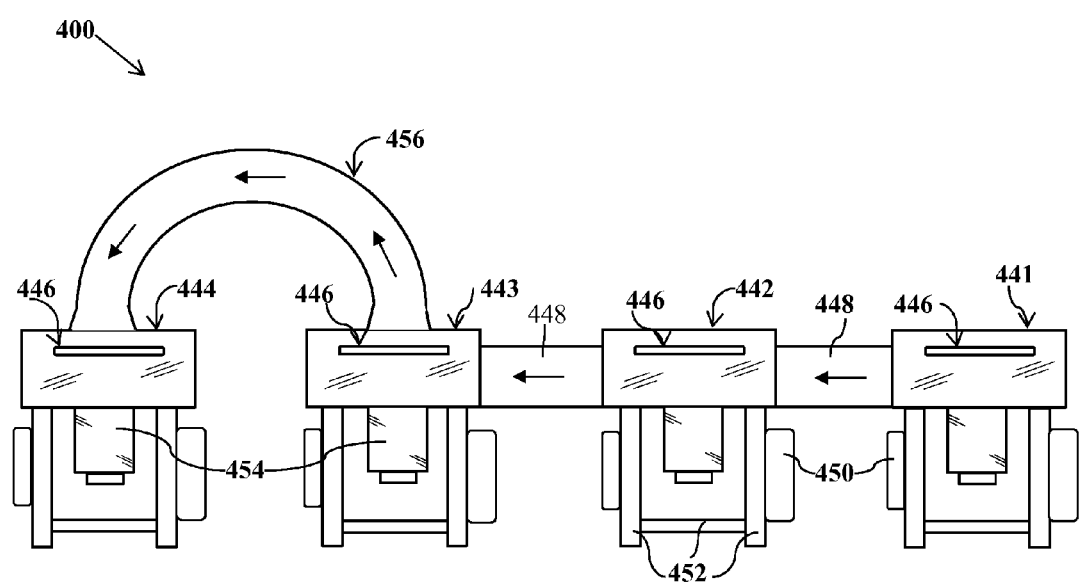
FIG. 4 illustrates side view of an exemplary system for manufacturing nanosized encapsulated drugs, according to an embodiment.

In general when the core drugs (i.e., the drugs to be encapsulated) have nanosized solid particle or crystals already available, then only encapsulation (one or more layers) of the nanosized drugs is needed using preferably only the fourth chamber (tumbler) 444 in FIG. 4. If the core drugs are in liquid form, nano filtering membrane processes are needed to form nanosized core drugs. And again, only fourth chamber 444 will preferably be used to coat the nanosized core drugs obtained through filtering.

If the core drugs are in molecular or gas form or even in solid/dust, or crystal/dust form, the below processes may be performed to shape up the nano drugs and to obtain the first layer of encapsulation (may not be completely enclosed), and thus, a solid shell nanosized drug capsule.

First (i.e., Step S51, FIG. 5), typically, wafers 330 (FIG. 3) made from glass, quartz or other suitable materials and having nanosized indents/cavities/dents 332 are produced. The size of the commonly used wafer at the moment is 300 mm, and the size is gradually shifting to 400 mm. The size of the dents is determined by the size of the nanosized drug that is needed. For example, the size of the dents may be as small as 20 nm. For intravenous administrated medicine, the size of the nanosized drug should be less than 200 nm. For surgically embedded medicine, it can be larger. Furthermore, the shape of the dents 332 may preferably be semispherical to allow easy removal of the nanosized drug from the dents.

Next, the indented wafer 330 is transported (Step S52, FIG. 5) into first chamber (deposition chamber) 441 (FIG. 4). A static electrode chuck (not shown) may be used to clamp the wafer 330 inside deposition chamber 441.

Next (Step S53, FIG. 5), protective material such as biodegradable polymer, is supplied into the deposition chamber 441 to form a first/bottom layer 334 of protective material that coats the wafer 330 including its dents 332 with a, for example, 5 nm thick coat 334. The polymer particles may be caused to be attracted toward the wafer 330 by an electrical field.

Figure 3:
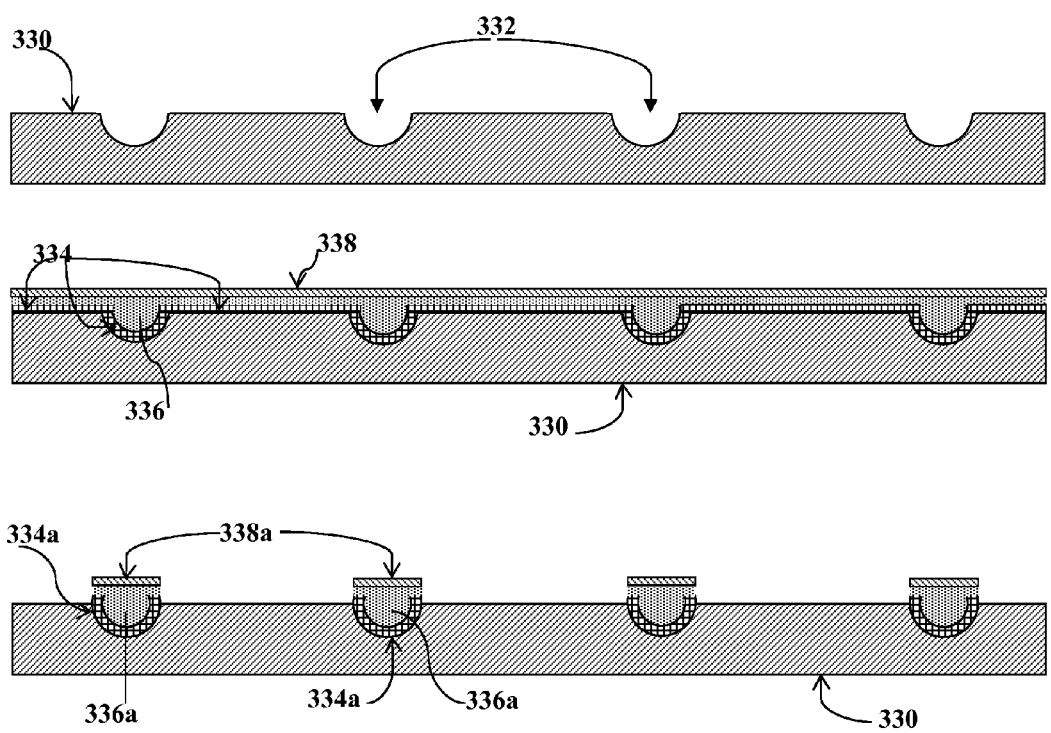
FIG. 3 illustrates sectional views of a wafer having nanosized dents, at different stages of the manufacturing process of nanosized encapsulated drugs, according to several embodiments.

Next, (Step S53, FIG. 5), the nanosized core drug 336 (FIG. 3) in gas, molecular or other form, is supplied to chamber 441 to fill the dents 332. The nanosized core drug in gas, molecular or other form may be supplied to chamber 441 together with other necessary agent(s) to fill the dents 332. During the deposition processes, chemical reaction and/or physical reaction may occur to form binding, form layers, or changing the gas to a non-gas form and/or form the small particles to the particle size of dents 332. These processes may be similar to the semiconductor deposition processes. It should be noted that, as shown in FIG. 3, the supplied nanodrug will typically also form a layer over the entire surface of the wafer 330, on top of first layer 334 of protective material.

Figure 5:
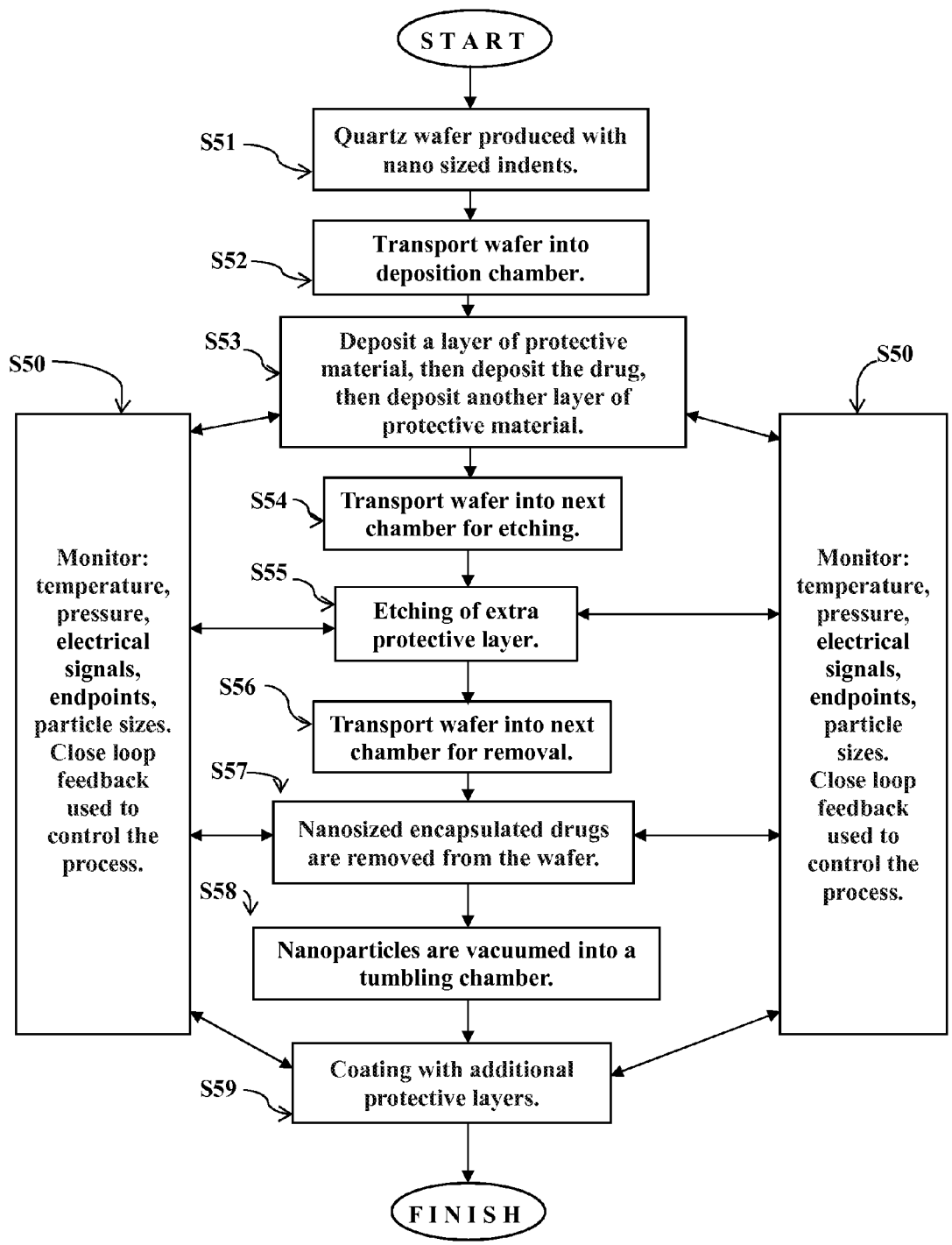
FIG. 5 is a flow chart depicting an exemplary process for manufacturing nanosized encapsulated drugs, according to an embodiment.

Next, still in Step S53, FIG. 5, protective material is supplied again into the deposition chamber 441 to form another (second/top) layer 338 of protective material to cover the core drugs 336. Typically, the entire wafer 330 will also be covered with the second layer 338 of protective material. Thus, the excess protective material and core drug resting on the wafer 330, outside of the area occupied by the dents 332, will have to be removed.

An exemplary method of polymer deposition is Plasma polymerization. When introducing molecular gases into a plasma, chemically active species are formed such as molecules in excited states, radicals and ions. These species can react with each other, neutral molecules or with the surface of a wafer. This results in deposition of a thin film. Films resulting from organic precursors are generally known as plasma polymers.

Next, (Step S54, FIG. 5), using transport module 448 (FIG. 4) wafer 330, containing the core drug 336 and the two layers (334, 338) of protective material as described above, is transported into the second/etching chamber 442 for removal of excess protective material and core drug. Before etching, pattern photoresist technique may be used to differentiate the locations to be etched away or to be retained. In the etching chamber 442, (Step S55, FIG. 5) the excessive areas are removed by selective etching method so as to leave a layer of protective material (334*a* and 338*a*, FIG. 3) mostly wrapped around the core drug 336*a* and all no dent areas cleared.

Next, (Step S56, FIG. 5), after the etching process, the wafer 330 is transported, using transport module 448 into the third/removal chamber 443 where the nanosized encapsulated drugs are removed (Step S57) from the wafer 330. The removal may be accomplished by, for example, using vacuum (Step S58) to draw the wrapped nanodrug, through the transport passage 456, into the fourth/tumbling chamber 444. For example, the use of temperature difference can be applied to cause the wafer dents to expand and the nano-encapsulated drugs to contract, thus, allowing the drugs to be easily moved off the wafer, namely from the dents 332. 3D vibration can also be used to separate the nano-encapsulated drugs from the wafer.

For the third/removal chamber 443, a pump is needed. For high vacuum level, a turbo pump is used. Sample of the turbo pump is BOC EDWARDS, PT6616050. In most cases, a normal pump is first used to get the vacuum down to the torr range and then the turbo pump takes the chamber to high vacuum level.

Thus, in chambers 441-443, the objective is to obtain a nanosized capsule from a drug that only exists in molecular or gas form. However, the process as described above in relation to chambers 441-443 may also be used to encapsulate nanodrugs available in other forms (e.g., solid small nanosized drug particles).

In the fourth chamber 444, (Step S59, FIG. 5), the nanosized drug capsules, already having one coat of protective material as explained above, may be coated with additional layers (one or more) of protective material. To accomplish this, in fourth chamber 444, the nanosized drug capsules may be supported by air, oxygen or any other bio allowable gas. The pressure of the supporting gas may be designed such that it can balance gravity by particle sizes, weight, and so on. Similarly, nanosized drug particles already existing in solid or crystal form may be processed directly in fourth chamber 444 (i.e., skipping chambers 441-443) for coating them with one more protective layers.

The nanocapsules transported from chamber 443 to chamber 444, or the already solid or crystal nanoparticles directly supplied to chamber 444, are coated with the additional protective layers in the chamber 444, by supplying encapsulation materials into the fourth chamber 444 together with supporting materials, and rotational and helical motions of the nanoparticles are caused by the fourth chamber (tumbler) 444 to close opened capsules, and to achieve uniform encapsulation. In the chamber 444, process conditions may be changed as needed to compress, smash, mesh, and or nest the bio-degradable coating material to construct certain physical formation or configuration such that core drugs are protected and drug release time is controlled.

For tumbler/blender 444, the preferred motor is an adjustable speed motor. One example of such a motor is DAYTON Adjustable Speed Motor.

It should be noted that during the entire encapsulation process, control systems 450 are used for each of the four chambers of the encapsulation system 400. Temperature controls, pressure controls, electrical signal controls, and so on, are designed into the system. Signal feedback loops are in place to control the encapsulation process (Step S50, FIG. 5).

Nanoscale scopes are installed on the viewports 446 so that the process can be monitored. Furthermore, as shown in FIG. 4, each chamber may be mounted on a frame 452 and each chamber may be equipped with a pump 454, or blower. Pump 454 will typically be used to create vacuum inside the chambers in order to create process condition needed and to draw the nanosized particles inside the chambers.

Online in-situ measurements and detection system are available.

The length of time the core drugs stay in the tumbler chamber are calculated/tested based on such factors as the release time needed, the protective material used, the physical configuration desired and/or the processing parameters (e.g., pressure, temperature, tumbling speed, possible layer configurations etc), which are controlled. For example, a first polymer (or other protective material) may be supplied to chamber 444 in which the temperature, pressure, tumbling speed and time are set particularly for this first polymer. Next, a second polymer of same or different properties may be supplied and the temperature, pressure, tumbling speed and time are set at different levels to achieve, for example, a different thickness of this layer. Similarly, a third polymer may be supplied, and so on.

EXAMPLE

Wafer size: 300 mm
Size of dent: 20-80 nm
Type of core drug: doxorubicin or topotecan or paclitaxel
Number of protective layers: 1 layer of polyhydroxyl butyrate or polycaprolactone or their copolymers.

The application of the above disclosed processes, methods, and systems, is not limited to medicine, pharmaceutical industries. They can be also used in other industries, such as the biotech, cosmetic and nutraceutical industries.

It may be advantageous to set forth definitions of certain words and phrases used in this patent document. The terms "include" and "comprise," as well as derivatives thereof, mean inclusion without limitation. The term "or" is inclusive, meaning and/or. The phrases "associated with" and "associated therewith," as well as derivatives thereof, may mean to include, be included within, interconnect with, contain, be contained within, connect to or with, couple to or with, be communicable with, cooperate with, interleave, juxtapose, be proximate to, be bound to or with, have, have a property of, or the like.

As used in this application, "plurality" means two or more. A "set" of items may include one or more of such items. Whether in the written description or the claims, the terms "comprising," "including," "carrying," "having," "containing," "involving," and the like are to be understood to be open-ended, i.e., to mean including but not limited to. Only the transitional phrases "consisting of" and "consisting essentially of," respectively, are closed or semi-closed transitional phrases with respect to claims. Use of ordinal terms such as "first," "second," "third," etc., in the claims to modify a claim element does not by itself connote any priority, precedence or order of one claim element over another or the temporal order in which acts of a method are performed. These terms are used merely as labels to distinguish one claim element having a certain name from another element having a same name (but for use of the ordinal term) to distinguish the claim elements. As used in this application, "and/or" means that the listed items are alternatives, but the alternatives also include any combination of the listed items.

Throughout this description, the embodiments and examples shown should be considered as exemplars, rather than limitations on the apparatus and procedures disclosed or claimed. Although many of the examples involve specific combinations of method acts or system elements, it should be understood that those acts and those elements may be combined in other ways to accomplish the same objectives.

With regard to flowcharts, additional and fewer steps may be taken, and the steps as shown may be combined or further refined to achieve the described methods. Acts, elements and features discussed only in connection with one embodiment are not intended to be excluded from a similar role in other embodiments.

One embodiment of the invention may be described as a process which is usually depicted as a flowchart, a flow diagram, a structure diagram, or a block diagram. Although a flowchart may describe the operations as a sequential process, many of the operations can be performed in parallel or concurrently. In addition, the order of the operations may be re-arranged. A process is terminated when its operations are completed. A process may correspond to a method, a program, a procedure, a method of manufacturing or fabrication, etc.

For means-plus-function limitations recited in the claims, if any, the means are not intended to be limited to the means disclosed in this application for performing the recited function, but are intended to cover in scope any means, known now or later developed, for performing the recited function.

The foregoing disclosure of the exemplary embodiments of the present invention has been presented for purposes of illustration and description. It is not intended to be exhaustive or to limit the invention to the precise forms disclosed. Many variations and modifications of the embodiments described herein will be apparent to one of ordinary skill in the art in light of the above disclosure. The scope of the invention is to be defined only by the claims appended hereto, and by their equivalents.

Further, in describing representative embodiments of the present invention, the specification may have presented the method and/or process of the present invention as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps set forth in the specification should not be construed as limitations on the claims. In addition, the claims directed to the method and/or process of the present invention should not be limited to the performance of their steps in the order written, and one skilled in the art can readily appreciate that the sequences may be varied and still remain within the spirit and scope of the present invention.

Although specific embodiments have been illustrated and described herein for the purpose of disclosing the preferred embodiments, someone of ordinary skills in the art will easily detect alternate embodiments and/or equivalent variations, which may be capable of achieving the same results, and which may be substituted for the specific embodiments illustrated and described herein without departing from the scope of the invention. Therefore, the scope of this application is intended to cover alternate embodiments and/or equivalent variations of the specific embodiments illustrated and/or described herein. Hence, the scope of the invention is defined by the accompanying claims and their equivalents. Furthermore, each and every claim is incorporated as further disclosure into the specification and the claims are embodiment(s) of the invention.

The foregoing examples have been provided merely for the purpose of explanation and are in no way to be construed as limiting of the present invention disclosed herein. While the invention has been described with reference to various embodiments, it is understood that the words, which have been used herein, are words of description and illustration, rather than words of limitation. Further, although the invention has been described herein with reference to particular means, materials, and embodiments, the invention is not intended to be limited to the particulars disclosed herein; rather, the invention extends to all functionally equivalent structures, methods and uses, such as are within the scope of the appended claims. Those skilled in the art, having the benefit of the teachings of this specification, may affect numerous modifications thereto and changes may be made without departing from the scope and spirit of the invention in its aspects.

I claim:

1. A process for manufacturing nanosized encapsulated drugs, comprising:
   placing a wafer comprising nanosized dents in a first chamber;
   supplying a protective material into the first chamber and applying a first layer of the protective material along a top surface of the wafer including said nanosized dents;
   supplying a nanosized core drug into the first chamber and applying a layer of the nanosized core drug on top of said first layer of protective material including filling said nanosized dents;
   supplying a protective material into the first chamber again and applying one or more additional layers of protective material on top of said layer of nanosized core drug, wherein type of said one or more additional layers of protective material is one of same as, and different from, said first layer of protective material, and wherein thickness of said one or more additional layers of protective material is one of same as, and different from, said first layer of protective material;
   transporting the wafer into a second chamber and removing excess of said first and said additional layers of protective material and excess of said nanosized core drug from the wafer, thereby ensuring that the nanosized core drug remains only in the nanosized dents substantially encapsulated by said first and said additional layers of protective material;
   transporting the wafer into a third chamber, and using one or more of a thermal expansion difference, a vibration, and a vacuum to pick up said substantially encapsulated nanosized drugs from said nanosized dents;
   transporting said picked up substantially encapsulated nanosized drugs through a passage into a fourth chamber; and
   supplying a protective material into said fourth chamber and applying one or more additional layers of said protective material around said substantially encapsulated nanosized drugs, wherein said protective material supplied into said fourth chamber is one of a same type and same thickness for each of said one or more additional layers, and different type and different thickness for said each of said one or more additional layers or any combination thereof, wherein type of said one or more additional layers of protective material applied in said fourth chamber is one of same as, and different from, type of said first layer of protective material and said additional layers of protective material applied in said first chamber, wherein thickness of said one or more additional layers of protective material applied in said fourth chamber is one of same as, and different from, thickness of said first layer of protective material and said additional layers of protective material applied in said first chamber, and wherein said applying of said one or more additional layers of said protective material in said fourth chamber further comprises providing one or more of a rotational motion and a helical motion to said substantially encapsulated nanosized drugs within said fourth chamber.

2. The process of claim 1, wherein the nanosized core drug is supplied into the first chamber in molecular or gaseous state.

3. The process of claim 1 wherein the nanosized core drug is supplied into the first chamber in solid/dust, or crystal/dust state.

4. The process of claim 1, wherein the protective material applied in said first chamber, and said fourth chamber is a polymer.

5. The process of claim 1, further comprising compressing, smashing, meshing, or nesting said applied layers of protective material to construct a predetermined physical configuration of said applied layers of protective material.

6. The process of claim 1, wherein processing parameters are monitored and controlled, and wherein said processing parameters that are controlled are at least one of a thickness of deposition of said nanosized core drug, said thickness of deposition of said first layer of protective material applied in said first chamber, said thickness of deposition of said one or more additional layers of protective material applied in said first chamber, and said thickness of deposition of said one or more additional layers of protective material applied in said fourth chamber.

7. The process of claim 6, wherein said monitoring and controlling of the processing parameters further comprises controlling said physical configuration of said applied layers of protective material.

8. The process of claim 6, wherein control systems are provided for each of said chambers, wherein said control systems are adapted for said monitoring of said processing parameters, wherein said control systems comprise one or more of a temperature controller, a pressure controller, and an electrical signal controller, and wherein signal feedback loops are provided for controlling said manufacturing process.

9. The process of claim 6, wherein each of said chambers comprises nanoscale scopes installed on viewports for said monitoring of said processing parameters.

10. The process of claim 1, wherein said each of said chambers are mounted on a frame, wherein one or more of said chambers are equipped with one of a pump and a blower, and wherein said pump is used to create said vacuum inside said each of said chambers.

11. The process of claim 1, wherein length of time said nano-encapsulated drugs stay in each of said chambers is determined based on factors comprising one or more of a release time of said nano-encapsulated drug when said nano-encapsulated drug is administered to a patient, said types of said protective materials used in said first and fourth chambers, a predetermined physical configuration of said applied layers of protective material, and a setting of processing parameters.

12. The process of claim 1, wherein said protective material applied in said first chamber, and said fourth chamber is selected from a group of aliphatic polymers comprising one of polyhydroxyl butyrate, polycaprolactone, and/or their copolymers.

13. The process of claim 1, wherein said nanosized core drug applied in said first chamber is selected from one of doxorubicin, topotecan, and paclitaxel.

14. A process for manufacturing nanosized encapsulated drugs, comprising:
    placing a wafer comprising nanosized dents in a first chamber;
    supplying a protective material into the first chamber and applying a first layer of the protective material along a top surface of the wafer including said nanosized dents, wherein said first layer of protective material is selected from a group of aliphatic polymers comprising one of polyhydroxyl butyrate, polycaprolactone, and/or their copolymers;
    supplying a nanosized core drug into the first chamber and applying a layer of the nanosized core drug on top of said applied first layer of protective material including filling said nanosized dents, wherein said nanosized core drug supplied into said first chamber is selected from one of doxorubicin, topotecan, and paclitaxel;
    supplying a protective material into the first chamber again and applying one or more additional layers of protective material on top of said applied layer of nanosized core drug, wherein type of protective material for said one or more additional layers is selected from a group of aliphatic polymers comprising one of polyhydroxyl butyrate, polycaprolactone, and/or their copolymers, and wherein type of, and thickness of said one or more additional layers of protective material is one of same as and different from said first layer of protective material;
    transporting the wafer into a second chamber and removing excess of said first and additional layers of protective material and excess of said nanosized core drug from the wafer, thereby ensuring that the nanosized core drug remains only in the nanosized dents substantially encapsulated by said first and said additional layers of protective material;
    transporting the wafer into a third chamber, and using one or more of a thermal expansion difference, a vibration, and a vacuum to pick up said substantially encapsulated nanosized drugs from said nanosized dents;
    transporting said picked up substantially encapsulated nanosized drugs through a passage into a fourth chamber; and
    supplying a protective material into said fourth chamber and applying one or more additional layers of protective material around said substantially encapsulated nanosized drugs, wherein said protective material supplied into said fourth chamber is selected from a group of aliphatic polymers comprising one of polyhydroxyl butyrate, polycaprolactone, and/or their copolymers, wherein said protective material supplied into said fourth chamber is one of a same type, and same thickness for each of said one or more additional layers or different type, and different thickness for said each of said one or more additional layers or any combination thereof, wherein type of, and thickness of said one or more additional layers of protective material applied in said fourth chamber is one of same as and different from type of, and thickness of said first layer of protective material and said additional layers of protective material applied in said first chamber, and wherein said applying of said one or more additional layers of said protective material to said substantially encapsulated nanosized drugs further comprises providing one or more of a rotational motion and a helical motion to said substantially encapsulated nanosized drugs within said fourth chamber.

* * * * *